United States Patent [19]

Langer et al.

[11] 4,218,466

[45] Aug. 19, 1980

[54] METHOD OF TREATING GASTRIC AND DUODENAL ULCERS

[75] Inventors: Salomon Z. Langer; Allan G. Roach, both of Paris, France

[73] Assignee: Synthelabo, Paris, France

[21] Appl. No.: 29,935

[22] Filed: Apr. 13, 1979

Related U.S. Application Data

[63] Continuation-in-part of Ser. No. 943,475, Sep. 18, 1978, abandoned.

[51] Int. Cl.$^2$ .............................................. A61K 31/38
[52] U.S. Cl. ..................................................... 424/275
[58] Field of Search ......................................... 424/275

[56] References Cited

FOREIGN PATENT DOCUMENTS 8199M 10/1968 France .

*Primary Examiner*—Stanley J. Friedman
*Attorney, Agent, or Firm*—Stevens, Davis, Miller & Mosher

[57] ABSTRACT

A method is provided for lowering the gastric acidity in the patient by administering to said patient an effective amount of 5-(2-dimethylamino-ethyl)-cis-2-(4-methoxyphenyl)-4-oxo-2,3-dihydro-5H-1,5-benzothiazepin-3-yl acetate or a pharmaceutically acceptable salt thereof to reduce said gastric acidity.

2 Claims, No Drawings

METHOD OF TREATING GASTRIC AND DUODENAL ULCERS

CROSS REFERENCE TO RELATED APPLICATION

This application is a continuation-in-part of Ser. No. 943,475, filed Sept. 18, 1978, now abandoned.

SUMMARY OF THE INVENTION

Gastric ulcers are treated by administering to a patient an effective amount of 5-(2-dimethylamino-ethyl)-cis-2-(4-methoxy-phenyl)-4-oxo-2,3-dihydro-5H-1,5-benzothiazepinacetate or a pharmaceutically acceptable salt thereof, e.g., the hydrochloride form. Another way of describing this activity is that the aforesaid compound has a histamine $H_2$-receptor antagonist activity.

DETAILED DESCRIPTION OF THE INVENTION 5-(2-dimethylamino-ethyl)-cis-2-(4-methoxy-phenyl)-4-oxo-2,3-dihydro-5H-1,5-benzothiazepin-3-yl acetate is produced in accordance with the disclosure of French Pat. No. 8199M, dated Oct. 25, 1968. This compound has been found effective for treating patients with excess gastric acid secretion, as confirmed in studies in rats. The favorable comparison with the known compound cimetidine shows the suitability of 5-(2-dimethylamino-ethyl)-cis-2-(4-methoxy-phenyl)-4-oxo-2,3-dihydro-5H-1,5-benzothiazepin-3-yl acetate as an effective agent for treating patients with excess gastric acid secretion. The preferred mode of administration is orally, such as by means of pills, capsules, or tablets. The daily dosage ranges from 90 to about 240 mg for an adult patient.

Verifying the utility of 5-(2-dimethylamino-ethyl)-cis-2-(4-methoxy-phenyl)-4-oxo-2,3-dihydro-5H-1,5-benzothiazepin-3-yl acetate for treating patients with gastric ulcer conditions, The animals were given 4 ml of saline (0.9% w/v NaCl in distilled water) orally and, then, anaesthetized with ether. After laparotomy, the gastric contents were removed via the duodenum by light compression of the stomach and the pylorus ligatured. Subsequently, either 5-(2-dimethylamino-ethyl)-cis-2-(4-methoxy-phenyl)-4'-oxo-2,3'-dihydro-5H-1,5'-benzacetate or cimetidine (10, 30 and 100 mg/kg) were administered (n=12/group) into the duodenum (i.d.) to study their effects on spontaneous gastric acid secretion. In other groups of animals (n=12), the effects of both drugs (100 mg/kg, i.d.) on histamine (20 mg/kg, s.c.) induced gastric acid secretion were accessed. Thereafter, the abdominal incision was closed and the animals were allowed to recover. Four hours later they were sacrificed with ether.

The oesophagus was ligatured, the stomach removed and incised to recuperate the contents, which were centrifuged. The volume of the gastric fluid was then measured.

Samples of supernatent were titrated with a solution of total (pH 8.5; phenolphthalein as indicator) acidities.

Results are given as $\mu$Eq of gastric acidity/100 g body weight and reported in Tables 1 and 2. The results show that both doses of 30 and 100 mg/kg intraduodenally of 5-(2-dimethylamino-ethyl)-cis-2-(4-methoxy-phenyl)-4-oxo-2,3-dihydro-5H-1,5-benzothiazepin-3-yl acetate and cimetidine similarly inhibited spontaneous gastric volume production and acidity. Therefore, 5-(2-dimethylamino-ethyl)-cis-2-(4-methoxy-phenyl)-4-oxo-2,3-dihydro-5H-1,5-benzothiazepin-3-yl acetate is as potent as cimetidine in reducing the spontaneous gastric acid secretion. The effect of 100 mg/kg intraduodenally of the compound on histamine induced gastric secretions were equivalent to that of the same dose of cimetidine. 5-(2-dimethylamino-ethyl)-cis-2-(4-methoxy-phenyl)-4-oxo-2,3-dihydro-5H-1,5-benzothiazepin-3-yl acetate may therefore be used for the treatment of peptic ulcer and stomach ailments due to hyperacidity.

In the following tables "A" is the hydrochloride form of 5-(2-dimethylamino-ethyl)-cis-2-(4-methoxy-phenyl)-4-oxo-2,3-dihydro-5H-1,5-benzothiazepin-3-yl acetate and "B" is cimetidine.

TABLE 1

Effects (means ± standard error of means) of several doses of cimetidine and diltiazem given intraduodenally on spontaneous gastric acid secretion.

| Group | Compound | mg/kg | Gastric volume ml/100 g | Free acidity $\mu$Eq/100 g | Total acidity $\mu$Eq/100 g |
|---|---|---|---|---|---|
| 1 | Distilled water | — | 2.19 ± 0.32 | 205 ± 43 | 234 ± 45 |
| 2 | B | 10 | 1.87 ± 0.26 | 155 ± 35 | 186 ± 38 |
| 3 | B | 30 | 1.27 ± 0.16 | 79 ± 15 | 106 ± 16 |
| 4 | B | 100 | 0.85 ± 0.09 | 22 ± 5 | 40 ± 8 |
| 5 | A | 10 | 1.70 ± 0.28 | 137 ± 35 | 170 ± 35 |
| 6 | A | 30 | 1.15 ± 0.29 | 89 ± 33 | 107 ± 35 |
| 7 | A | 100 | 0.36 ± 0.06 | 16 ± 6 | 26 ± 8 |

TABLE 2

Effects (means ± standard error of means) of diltiazem and cimetidine (100 mg/kg intraduodenally) on histamine induced gastric secretion in rats (n = 12/group).

| Group | Histamine (mg/kg) s.c. | Compound | mg/kg | Gastric volume ml/100 g | Free acidity $\mu$Eq/100 g | Total acidity $\mu$Eq/100 g |
|---|---|---|---|---|---|---|
| 1 | — | — | | 2.47 ± 0.37 | 220 ± 48 | 255 ± 55 |
| 2 | 20 | — | | 3.15 ± 0.38 | 336 ± 58 | 380 ± 62 |
| 5 | 20 | B | 100 | 1.20 ± 0.18 | 57 ± 13 | 73 ± 17 |
| 8 | 20 | A | 100 | 1.08 ± 0.16 | 72 ± 21 | 92 ± 22 |

It is seen that the above tests demonstrate a histamine $H_2$-receptor antagonist activity thus establishing the suitability of the tested compound for treatment of gastric ulcers.

Guinea pigs of either sex (Hartley, 350-450 g) were sacrificed by cervical fracture. The whole heart was immediately removed from the thoracic cavity and immersed in oxygenated (95% $O_2$ and 5% $CO_2$) salt solution (NaCl, 120; KCl, 5.6; $CaCl_2$, 2.2; $MgCl_2$, 2.1; $NaH_2PO_4$ 1.2; $NaHCO_3$, 25.0; glucose 10.0 mM). The left and the right atria were separately dissected free of all extraneous tissue. The base of the right auricle was attached to a tissue holder and a thread was passed through the tip of each atria. The preparations were then transferred to a tissue bath containing 30 ml of the above oxygenated salt solution (at 31° C.) and connected by the thread to a Grass FT.03 force displacement transducer.

The control average tension was 0,5 g. The right atrium was allowed to beat spontaneously.

An equilibrium period of 60 min was allowed before experimental procedures were begun.

Exposure of right guinea pig atria to histamine (1.0 μM) induced a sustained positive chronotropic response.

Diltiazem (0,04 μM9), cimetidine (0.3 μM) or their solvent (salt solution) were studied against histamine in this preparation.

In 3 groups of guinea pig atria used to study diltiazem (0.04 μM), cimetidine (0.3 μM) or their solvent (salt solution), the initial spontaneous beating rates were 123±10, 119±8 and 95±3 beats/min, respectively. Addition of histamine (1.0 μM) induced respective atrial Under control conditions this peak response persisted for 45 min.

Diltiazem (0.04 μM) and cimetidine (0.3 μM) produced equivalent reductions of the positive chronotropic effects of histamine.

Therefore, diltiazem seems to be more active than cimetidine as histamine $H_2$-receptor antagonist.

What is claimed and intended to be secured by Letters Patent is:

1. A method of lowering the gastric acidity in a patient having excess gastric acidity by orally administering to said patient an effective amount of 5-(2-dimethylamino-ethyl)-cis-2-(4-methoxy-phenyl)-4-oxo-2,3-dihydro-5H-1,5-benzothiazepin-3-yl said gastric acidity.

2. A method of providing a patient with histamine $H_2$- receptor antagonist activity which comprises orally administering to a patient requiring such activity an effective amount of 5-(2-dimethylamino-ethyl)-cis-2-(4-methoxy-phenyl)-4-oxo-2,3-dihydro-5H-1,5-benzothiazepin-3-yl acetate or a pharmaceutically acceptable salt thereof to provide said histamine $H_2$-receptor antagonist activity.

* * * * *